(12) United States Patent
Xu (10) Patent No.: US 7,961,304 B2
(45) Date of Patent: Jun. 14, 2011

(54) OPTICAL DEVICE COMPONENTS

(75) Inventor: Zhi Xu, St. Louis, MO (US)

(73) Assignee: The Curators of the University of Missouri, Columbia, MO (US)

(*) Notice: Subject to any disclaimer, the term of this patent is extended or adjusted under 35 U.S.C. 154(b) by 165 days.

(21) Appl. No.: 12/209,807

(22) Filed: Sep. 12, 2008

(65) Prior Publication Data

US 2009/0079964 A1    Mar. 26, 2009

Related U.S. Application Data

(60) Provisional application No. 60/972,121, filed on Sep. 13, 2007.

(51) Int. Cl.
*G01N 33/48* (2006.01)

(52) U.S. Cl. .......................... 356/39; 600/322; 362/154

(58) Field of Classification Search ............... 356/39–40, 356/436–440; 600/310, 318, 316, 319; 362/154, 362/247, 298, 304, 346, 302, 303
See application file for complete search history.

(56) References Cited

U.S. PATENT DOCUMENTS

| | | | | |
|---|---|---|---|---|
| 2,441,343 A | * | 5/1948 | Becker | .......................... 356/394 |
| 3,621,268 A | * | 11/1971 | Friedrich et al. | ........... 250/214.1 |
| 3,954,560 A | | 5/1976 | Delafosse et al. | |
| 3,963,327 A | | 6/1976 | Poirier | |
| 4,014,321 A | | 3/1977 | March | |
| 4,632,559 A | | 12/1986 | Brunsting | |
| 4,655,225 A | | 4/1987 | Dahne et al. | |
| 4,781,195 A | | 11/1988 | Martin | |
| 4,962,311 A | * | 10/1990 | Poisel et al. | ................... 250/216 |
| 4,997,769 A | | 3/1991 | Lundsgaard et al. | |
| 5,009,230 A | | 4/1991 | Hutchinson | |
| 5,028,787 A | | 7/1991 | Rosenthal et al. | |
| 5,077,476 A | | 12/1991 | Rosenthal | |
| 5,086,229 A | | 2/1992 | Rosenthal et al. | |
| 5,112,124 A | | 5/1992 | Harjunmaa et al. | |
| 5,137,023 A | | 8/1992 | Mendelson et al. | |
| 5,183,042 A | | 2/1993 | Harjunmaa et al. | |
| 5,222,496 A | | 6/1993 | Clarke et al. | |
| 5,255,171 A | * | 10/1993 | Clark | ............................ 362/231 |
| 5,423,983 A | | 6/1995 | Chiang et al. | |
| 5,529,065 A | | 6/1996 | Tsuchiya | |
| 5,535,743 A | | 7/1996 | Backhaus et al. | |

(Continued)

FOREIGN PATENT DOCUMENTS

EP    01094745 A1    5/2001

(Continued)

OTHER PUBLICATIONS

International Search Report for PCT/US2008/010670 dated Nov. 21, 2008.

(Continued)

*Primary Examiner* — Hoa Q Pham
(74) *Attorney, Agent, or Firm* — Thompson Coburn LLP (57) ABSTRACT

Embodiments of the invention relate to a light illumination funnel. The funnel includes a first opening positioned to receive an incoming light source, a second opening positioned opposite the first opening and with a diameter smaller than the first opening and inner reflective walls, in contact with the first opening and second opening. The funnel has a half angle of less than 25 degrees. Embodiments also relate to a light collection funnel and an apparatus utilizing both a light illumination funnel and light collection funnel.

21 Claims, 7 Drawing Sheets

U.S. PATENT DOCUMENTS

| | | | |
|---|---|---|---|
| 5,553,613 A | 9/1996 | Parker | |
| 5,576,544 A | 11/1996 | Rosenthal | |
| 5,615,672 A | 4/1997 | Braig et al. | |
| 5,615,673 A | 4/1997 | Berger et al. | |
| 5,666,956 A | 9/1997 | Buchert | |
| 5,671,301 A | 9/1997 | Kupershmidt | |
| 5,703,364 A | 12/1997 | Rosenthal | |
| 5,743,262 A | 4/1998 | Lepper, Jr. et al. | |
| 5,910,109 A | 6/1999 | Peters et al. | |
| 6,025,597 A | 2/2000 | Sterling et al. | |
| 6,043,492 A | 3/2000 | Lee et al. | |
| 6,064,898 A | 5/2000 | Aldrich | |
| 6,097,975 A | 8/2000 | Petrovsky et al. | |
| 6,134,458 A | 10/2000 | Rosenthal | |
| 6,151,517 A | 11/2000 | Honigs et al. | |
| 6,181,958 B1 | 1/2001 | Steuer et al. | |
| 6,205,354 B1 | 3/2001 | Gellermann et al. | |
| 6,208,788 B1 | 3/2001 | Nosov | |
| 6,304,767 B1 | 10/2001 | Soller et al. | |
| 6,312,393 B1 | 11/2001 | Abreu | |
| 6,337,564 B2 | 1/2002 | Manzini et al. | |
| 6,403,944 B1 | 6/2002 | MacKenzie et al. | |
| 6,421,548 B1 | 7/2002 | Berman et al. | |
| 6,424,848 B1 | 7/2002 | Berman et al. | |
| 6,424,849 B1 | 7/2002 | Berman et al. | |
| 6,424,851 B1 | 7/2002 | Berman et al. | |
| 6,430,424 B1 | 8/2002 | Berman et al. | |
| 6,445,938 B1 | 9/2002 | Berman et al. | |
| 6,522,903 B1 | 2/2003 | Berman et al. | |
| 6,574,490 B2 | 6/2003 | Abbink et al. | |
| 6,671,528 B2 | 12/2003 | Steuer et al. | |
| 6,684,099 B2 | 1/2004 | Ridder et al. | |
| 6,723,048 B2 | 4/2004 | Fuller | |
| 6,731,963 B2 | 5/2004 | Finarov et al. | |
| 6,775,564 B1 | 8/2004 | Peters et al. | |
| 6,804,002 B2 | 10/2004 | Fine et al. | |
| 6,833,540 B2 | 12/2004 | MacKenzie et al. | |
| 6,865,408 B1 | 3/2005 | Abbink et al. | |
| 6,873,865 B2 | 3/2005 | Steuer et al. | |
| 6,958,039 B2 | 10/2005 | Burd et al. | |
| 6,968,222 B2 | 11/2005 | Burd et al. | |
| 6,990,365 B1 | 1/2006 | Parker et al. | |
| 6,993,372 B2 | 1/2006 | Fine et al. | |
| 7,039,447 B2 | 5/2006 | Berman et al. | |
| 7,043,289 B2 | 5/2006 | Fine et al. | |
| 7,107,087 B2 | 9/2006 | Hwang et al. | |
| 7,133,711 B2 | 11/2006 | Chernoguz et al. | |
| 7,254,432 B2 | 8/2007 | Fine | |
| 7,266,400 B2 | 9/2007 | Fine et al. | |
| 7,409,239 B2 | 8/2008 | Chung et al. | |
| 7,424,317 B2 | 9/2008 | Parker et al. | |
| 2001/0030742 A1* | 10/2001 | Kramer et al. | 356/72 |
| 2001/0039376 A1 | 11/2001 | Steuer et al. | |
| 2002/0010563 A1 | 1/2002 | Ratteree et al. | |
| 2002/0016534 A1 | 2/2002 | Trepagnier et al. | |
| 2002/0019055 A1 | 2/2002 | Brown et al. | |
| 2002/0161289 A1 | 10/2002 | Hopkins et al. | |
| 2002/0167704 A1* | 11/2002 | Kleinhans et al. | 359/176 |
| 2003/0004423 A1 | 1/2003 | Lavie et al. | |
| 2003/0023152 A1 | 1/2003 | Abbink et al. | |
| 2003/0078504 A1 | 4/2003 | Rowe | |
| 2004/0087844 A1 | 5/2004 | Yen | |
| 2004/0106163 A1 | 6/2004 | Workman et al. | |
| 2004/0127779 A1 | 7/2004 | Steuer et al. | |
| 2004/0181132 A1 | 9/2004 | Rosenthal | |
| 2004/0225205 A1 | 11/2004 | Fine et al. | |
| 2004/0225206 A1 | 11/2004 | Kouchnir | |
| 2005/0131286 A1 | 6/2005 | Parker et al. | |
| 2005/0272987 A1 | 12/2005 | Kiani-Azarbayjany et al. | |
| 2006/0009685 A1 | 1/2006 | Finarov et al. | |
| 2006/0058622 A1 | 3/2006 | Tearney et al. | |
| 2006/0063983 A1 | 3/2006 | Yamakoshi | |
| 2006/0129040 A1 | 6/2006 | Fine et al. | |
| 2006/0152726 A1 | 7/2006 | Larsen et al. | |
| 2006/0200014 A1 | 9/2006 | Fine et al. | |
| 2006/0224057 A1 | 10/2006 | Burd et al. | |
| 2006/0226992 A1 | 10/2006 | Al-Ali et al. | |
| 2006/0250676 A1 | 11/2006 | Hagood | |
| 2006/0258918 A1 | 11/2006 | Burd et al. | |
| 2006/0264719 A1 | 11/2006 | Schurman et al. | |
| 2007/0078312 A1 | 4/2007 | Fine et al. | |
| 2007/0149869 A1 | 6/2007 | Yen | |
| 2008/0027297 A1 | 1/2008 | Yamakoshi | |
| 2008/0144004 A1 | 6/2008 | Rosenthal | |
| 2008/0194014 A1* | 8/2008 | Young et al. | 435/288.1 |
| 2009/0059586 A1* | 3/2009 | Livesay et al. | 362/247 |
| 2009/0105565 A1* | 4/2009 | Xu | 600/310 |
| 2009/0116017 A1* | 5/2009 | Xu et al. | 356/436 |
| 2009/0196025 A1* | 8/2009 | Joseph et al. | 362/154 |
| 2009/0270700 A1 | 10/2009 | Van Herpen et al. | |
| 2010/0026995 A1 | 2/2010 | Merritt et al. | |

FOREIGN PATENT DOCUMENTS

| | | |
|---|---|---|
| WO | 90/13092 A1 | 11/1990 |
| WO | 9115991 A1 | 10/1991 |
| WO | 9115992 A1 | 10/1991 |
| WO | 9300856 A1 | 1/1993 |
| WO | 93/06774 A1 | 4/1993 |
| WO | 9413199 A1 | 6/1994 |
| WO | 9416614 A1 | 8/1994 |
| WO | 9531930 A1 | 11/1995 |
| WO | 9604840 A1 | 2/1996 |
| WO | 9617546 A1 | 6/1996 |
| WO | 9639927 A1 | 12/1996 |
| WO | 9803847 A2 | 1/1998 |
| WO | 9836681 A1 | 8/1998 |
| WO | 9939631 A1 | 8/1999 |
| WO | 0001294 A1 | 1/2000 |
| WO | 0016688 A1 | 3/2000 |
| WO | 0193755 A1 | 12/2001 |
| WO | 0196872 A2 | 12/2001 |
| WO | 02082990 A1 | 10/2002 |
| WO | 03010510 A2 | 2/2003 |
| WO | 2005045377 A2 | 5/2005 |
| WO | 2006086566 A2 | 8/2006 |
| WO | 2006094109 A1 | 9/2006 |
| WO | 2007122557 A2 | 11/2007 |
| WO | 2008/039195 A1 | 4/2008 |
| WO | 2010017238 A1 | 2/2010 |

OTHER PUBLICATIONS

International Search Report for PCT/US2008/011438 dated Dec. 9, 2008.
Wagner et al., "Invasiveness as a Barrier to Self-Monitoring of Blood Glucose in Diabetes", Diabetes Technology & Therapeutics, Aug. 1, 2005.
Web Page Document entitled http://www.orsense.com/Diabetes_Monitoring dated Aug. 9, 2007.
International Preliminary Report on Patentability (Chapter II) for PCT/US2008/011438 dated Jun. 18, 2010.
International Search Report and Written Opinion for PCT/US2010/028255 dated May 19, 2010.
Office Action for U.S. Appl. No. 12/256,028 dated May 24, 2010.
Office Action for U.S. Appl. No. 12/209,807 dated May 17, 2010.
International Preliminary Report on Patentability (Chapter II) for PCT/US2009/040942 dated Dec. 13, 2010.
International Preliminary Report on Patentability (Chapter II) for PCT/US2009/037805 dated Dec. 14, 2010.
Office Action for U.S. Appl. No. 12/256,028 dated Sep. 15, 2010.

* cited by examiner

(PRIOR ART)

OPTICAL DEVICE COMPONENTS

PRIORITY OF INVENTION

This non-provisional application claims the benefit of priority under 35U.S.C. §119(e) to U.S. Provisional Patent Application Ser. No. 60/972,121, filed Sep. 13, 2007, which is herein incorporated by reference in its entirety.

BACKGROUND

A fundamental property of a sample, whether it is a gas, liquid or solid, is its tendency or lack of tendency to absorb or scatter light at certain wavelengths. Characterization of the tendency of a sample to absorb, scatter or transmit is the basis for many optical measurements and instrumentation (e.g., spectrophotometry). The accuracy and repeatability of measurements taken with optical devices relates to many factors, including the strength of signal reaching one or more detectors. Optical devices may be used to measure the presence and quantities of components in human or animal blood or interstitial fluid. In one example, a non-invasive optical apparatus may use some form of spectroscopy to acquire the signal or spectrum from a target area of a body of the user.

The American Diabetes Association reports that over six percent (6%) of Americans, more than 17 million people, have diabetes. According to scientists with the Centers for Disease Control ("CDC"), one in three children born in the United States in year 2000 will become diabetic unless many more people start eating less and exercising more. One CDC study revealed that there were approximately 11 million diagnosed cases of diabetes in 2000 and that the number of diagnosed cases could rise to 29 million by the year 2050.

A vital element of diabetes management is the self-monitoring of blood glucose concentration by diabetics in the home environment. However, current monitoring techniques discourage regular use due to the inconvenient and painful nature of drawing blood or interstitial fluid through the skin prior to analysis. As a result, non-invasive measurement of glucose concentration is a desirable and beneficial development for the management of diabetes.

There exist a number of non-invasive approaches for blood glucose determination. One technique of non-invasive blood chemicals detection involves collecting and analyzing light spectra data. Extracting information about blood characteristics such as glucose concentration from spectral or other data obtained from spectroscopy is a complex problem due to the presence of components (e.g., skin, fat, muscle, bone, interstitial fluid) other than blood in the area that is being sensed. Such other components can influence these signals in such a way as to alter the reading. In particular, the resulting signal may be much larger in magnitude than the portion of the signal that corresponds to blood, and therefore limits the ability to accurately extract blood characteristics information.

SUMMARY

Embodiments of the invention relate to a light illumination funnel. The funnel includes a first opening positioned to receive an incoming light source, a second opening positioned opposite the first opening and with a diameter smaller than the first opening and inner reflective walls, in contact with the first opening and second opening. The funnel has a half angle of less than 25 degrees.

Embodiments relate to a light collection funnel, including a first opening positioned to receive an incoming sample light source, a second opening positioned opposite the first opening and with a diameter larger than the first opening and inner reflective walls in contact with the first opening and second opening.

Embodiments also relate to an apparatus, including a light source configured to generate a plurality of light beams, each of the plurality of light beams having a different wavelength range, a light illumination funnel for collecting the plurality of light beams through an entrance opening having a first diameter and for focusing and directing the plurality of light beams to the target area through an exit opening having a second diameter, wherein the second diameter is less than the first diameter. The apparatus also includes a light collection funnel for collecting the plurality of light beams emitting from the target area at a second entrance opening having a third diameter and for directing the plurality of light beams through a second exit opening having a fourth diameter, wherein the third diameter is less than the fourth diameter, a detector comprising a plurality of light-sensing devices each configured to detect a light beam directed through the second exit opening and to generate an output signal indicative of the power of light detected and a processor for analyzing the output signal and generating measurement data.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the present invention is defined by the appended claims and their equivalents.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

Embodiments of the present invention relate to optical components, such as light funnels for illumination and measurement of optical properties of a sample. Although spectroscopic sampling of human or animal body regions are exemplified, the embodiments relate to all types of optical instrumentation, including optical detectors, microscopes, spectrometers, etc. Optical spectroscopy can be used to determine the amount of light absorbed by a biological sample such as human finger. By measuring the amount of light absorbed by the finger, it is possible to determine glucose, cholesterol, and hemoglobin levels of a person non-invasively. Fingertip measurements are usually preferred because of the large concentration of capillaries in the fingertip and because of the conversion of arterial blood into venous blood that occurs in the fingertip.

Figure 1A:
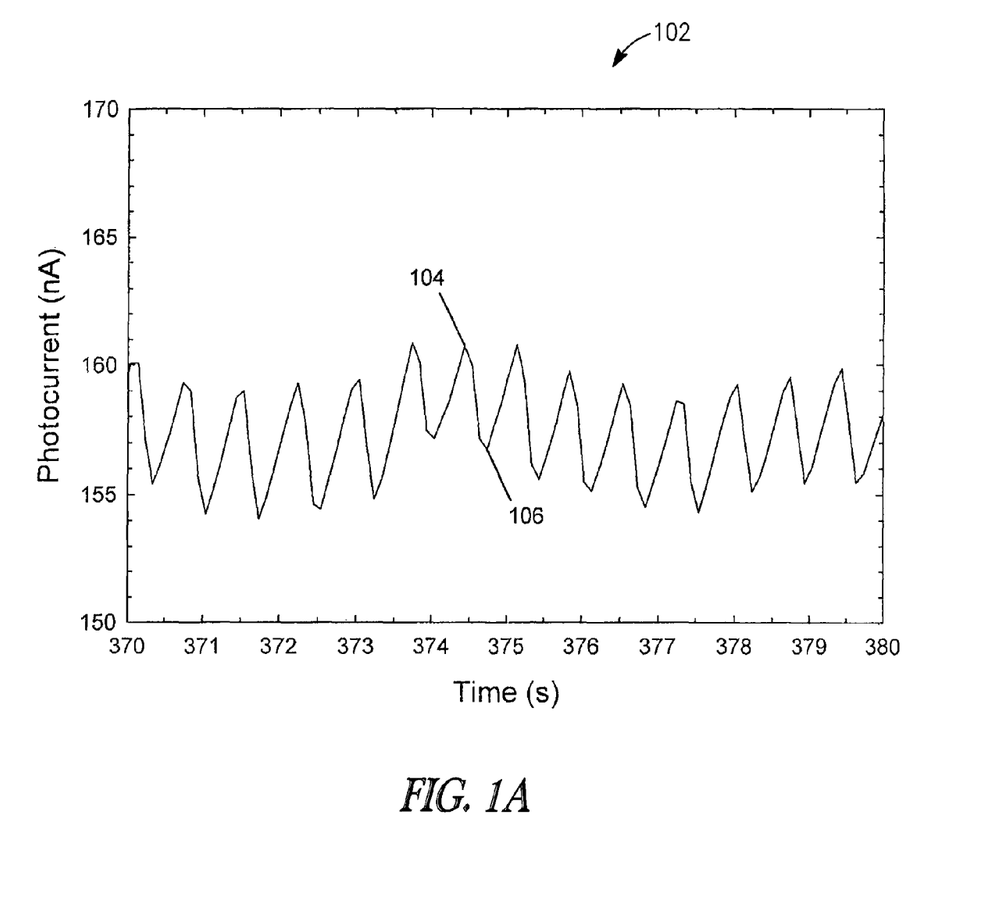
FIGS. 1A-B illustrate plots of a pulse wave corresponding to light absorption of arterial blood, according to some embodiments.

When light is transmitted through a biological sample, such as a human finger, the light is absorbed and scattered by various components of the finger including skin, muscle, bone, fat, interstitial fluid and blood. It has been observed, however, that light absorption by a human finger exhibits a small cyclic pattern that corresponds to a heartbeat. FIG. 1A depicts a plot 102 of a pulse wave that corresponds to the light absorption of arterial blood in the capillary due to the heartbeat of the user. Although the magnitude of the cyclic pattern is small in comparison to the total photocurrent generated by the detector, considerable information can be extracted from the cyclic pattern of the plot 102. For example, assuming that the person's heart rate is sixty beats per minute, the time between the start of any pulse beat and the end of that pulse beat is one-second. During this one-second period, the plot will have a maximum or peak 104 reading and minimum or valley 106 reading. The peak 104 reading of the plot corresponds to when there is a minimum amount of blood in the capillaries, and the valley 106 reading corresponds to when there is a maximum amount of blood in the capillaries. By using optical information provided by the peak and valley of the cyclic plot, the optical absorption and scattering by major finger constituents that are not in the capillaries such as skin, fat, bones, muscle and interstitial fluids are excluded. These major constituents that are not in the capillaries are excluded because they are not likely to change during the one-second interval. In other words, the light that is absorbed by the blood can be detected based on the peaks and valleys of the plot 102.

Assuming the peak of the cyclic photo current generated by the light-sensing device is $I_P$, the adjacent valley of the cyclic photo current is $I_V$, and the photo current generated by the light-sensing device without a human finger is $I_0$, the transmittances corresponding to the peak and valley photo currents can be defined as:

$$T_V = \frac{I_V}{I_0}; \quad (1)$$

and $$T_P = \frac{I_P}{I_0}; \quad (2)$$

The corresponding peak and valley absorbance are:

$$A_V = -\log(T_V) \quad (3);$$

and $$A_P = -\log(T_P) \quad (4);$$

The difference between $A_V$ and $A_P$ reflects the light absorption and scattering by only the blood in the finger:

$$\Delta A = A_V - A_P = \log\left(\frac{I_P}{I_V}\right); \quad (5)$$

The algorithms shown in equation (5) only require monitoring the change in photo current to determine a change in light power transmitted through the finger. As a result, there is no need to determine photo current generated by the light-sensing device without a human finger.

Figure 1B:
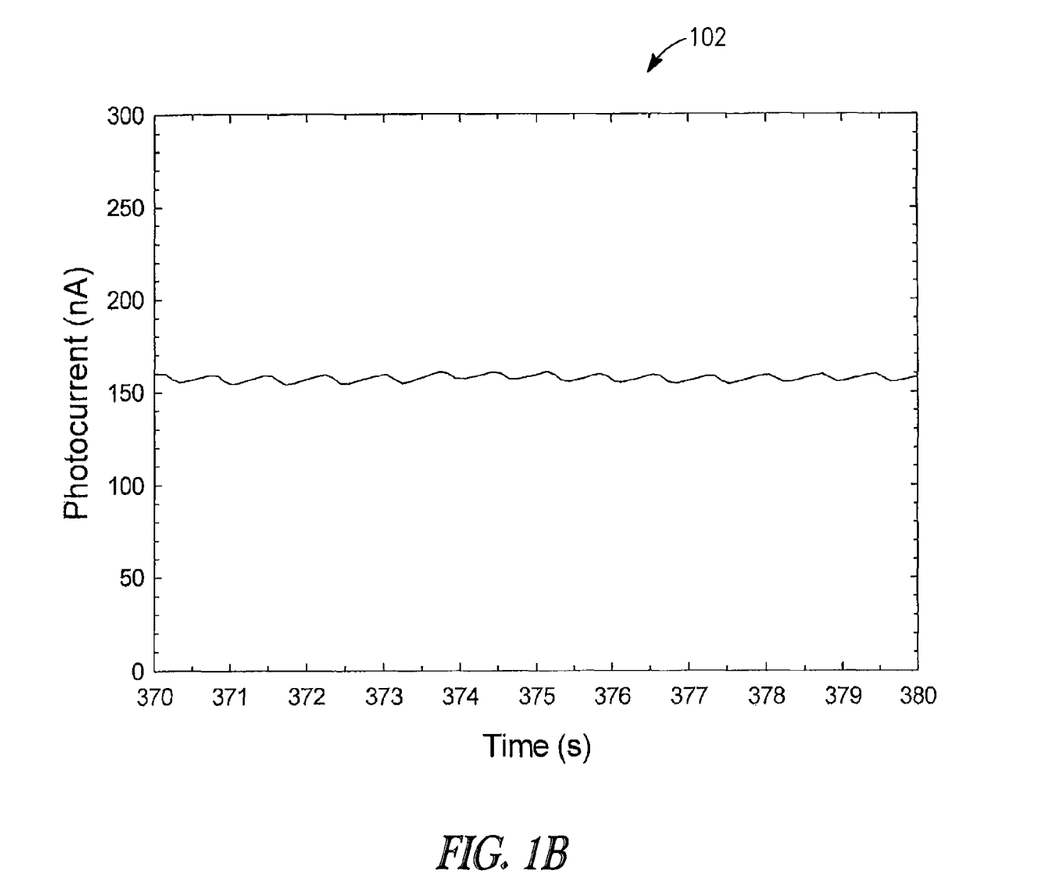

Unfortunately, because the cyclic pattern is a very small signal, the amplitude of cyclic pattern (i.e., the difference between peak and valley) is typically 1%-3% of the total light power transmitted through the finger. FIG. 1A illustrates the cyclic pattern on a magnified scale. FIG. 1B depicts a more accurate reflection of the cyclic pattern in terms of signal amplitude. To obtain a signal to noise (S/N) ratio of 100:1 in the determination of $\Delta A$, the baseline noise of the device being used to measure the light absorption by the finger should not be larger than $3.0\times10^{-5}$ in absorbance (peak to peak), within a 10 Hz bandwidth.

However, a $3.0\times10^{-5}$ absorbance (peak to peak) baseline noise level within a 10 Hz bandwidth is difficult to obtain with the low light power levels that are used by some battery powered hand held non-invasive blood chemicals measurement devices. One solution involves increasing light illumination power. However, due to size limitations of some devices, it may not be possible or it may be inefficient to increase illumination power to achieve a desired baseline noise level (e.g., battery drain). Thus, there is a need for a system and method to increase the amount light power that can be detected by such devices without significantly increasing device size and battery power consumption.

Figure 2:
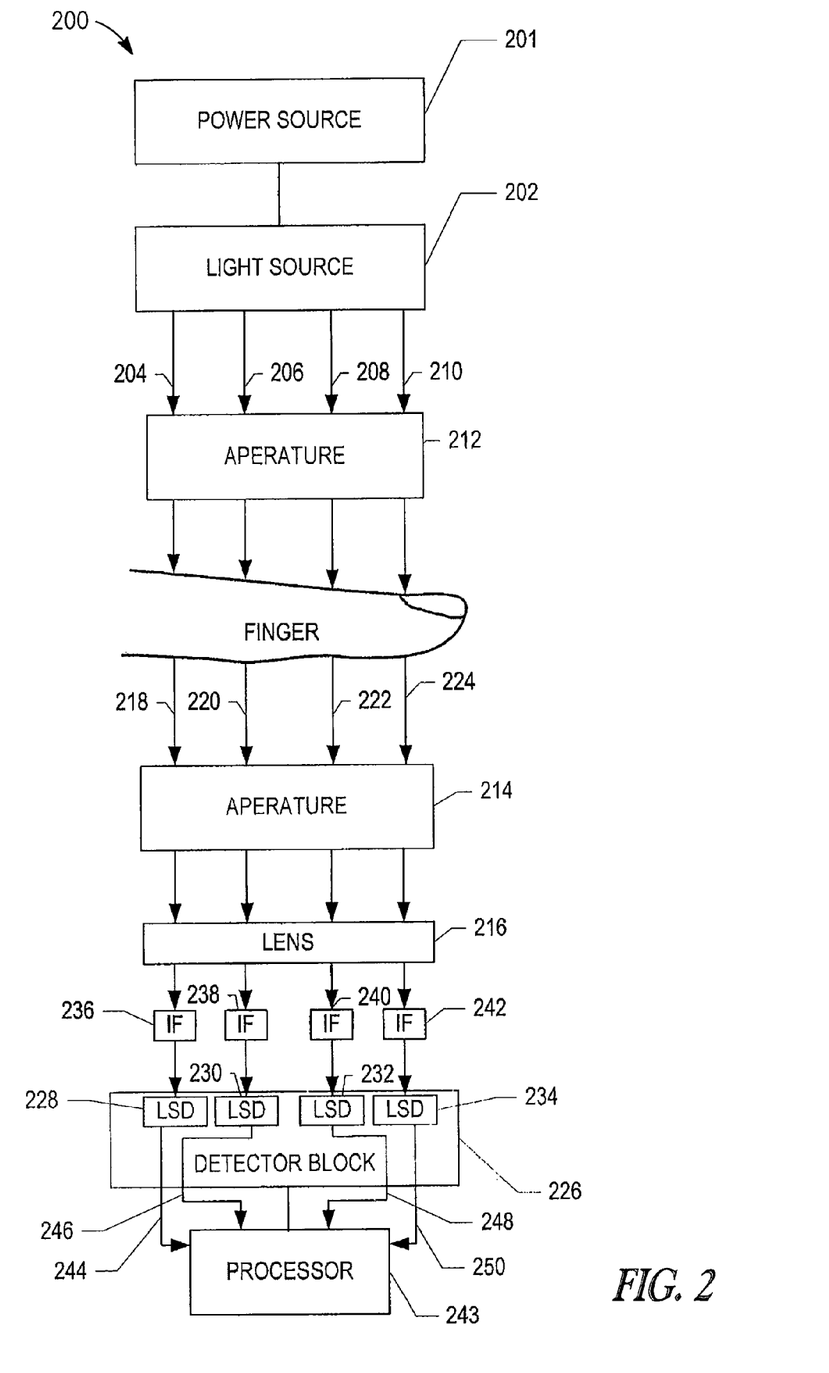
FIG. 2 illustrates an optical configuration, according to some embodiments.

FIG. 2 is a simplified block diagram that illustrates components of a current optical measurement system 200 that uses the "pulsatile" concept for determining an amount of light absorbed and scattered solely by the blood in a human finger. A power source 201, such as a battery, provides power to a light source 202 that generates a plurality of light beams 204, 206, 208, 210 that are directed toward the top of the finger of a user. According to one aspect of the optical measurement system 200, each of the light beams 204, 206, 208, 210 have a different wavelength or a different wavelength range, typically within 800 nm to 1800 nm. For example, the first light beam 204 may have a wavelength range between 850-900 nanometers ("nm"), the second light beam 206 may have a wavelength range between 875-940 nm, the third light beam 208 may have a wavelength between 920-980 nm, and the fourth light beam 210 may have a wavelength between 950-1050 nm. Although the optical measurement system 200 is described herein as generating four (4) light beams, it is contemplated that the light source 202 can be altered to generate fewer light beams or additional light beams in other embodiments.

A first aperture 212 ensures that the light beams 204, 206, 208, 210 strike a target area of the finger. A second aperture 214 ensures that the portion of the light beams that are transmitted through the finger strike a lens 216. Light beams 204, 206, 208, 210 are attenuated by the finger and components of the optical measurement system 200, and, thus, attenuated light beams 218, 220, 222, 224 are emitted from the finger. The attenuated light beams 218, 220, 222, 224 strike the lens 216, and the lens 216 collects the attenuated light beams 218, 220, 222, 224 so that they impinge more efficiently on a detector block 226.

The detector block 226 is positioned directly under the lens 216 and comprises a plurality of light-sensing devices (LSD) 228, 230, 232, 234 such as an array of photodiodes. According to one aspect of the optical measurement system 200, each of the light-sensing devices 228, 230, 232, 234 detects a specific wavelength of light as defined by corresponding interference filters 236, 238, 240, 242, respectively. The interference filter transmits one or more spectral bands or lines of light, and blocks others.

Each of the light-sensing devices 228, 230, 232, 234 generates a corresponding current signal that is proportional to the power of the light received by the particular light sensing device. The current signal generated by the photodiode can be converted to another form of signal, such as an analog voltage signal or a digital signal.

A processor 243 is coupled to the detector block 226 and is configured to calculate the change of photo current signals 244, 246, 248, 250.

According to one aspect, the processor 243 executes an algorithm such as shown in the equation (5) to calculate the change in the light absorption ($\Delta A$) solely caused by the blood in the finger. Thereafter, this quantitative calculation of light absorption of the blood can be used to determine a characteristic of the blood. For example, by comparing the calculated light absorption value to predetermined values corresponding to different glucose levels stored in a memory (not shown), a glucose level of the user can be determined.

Figure 3:
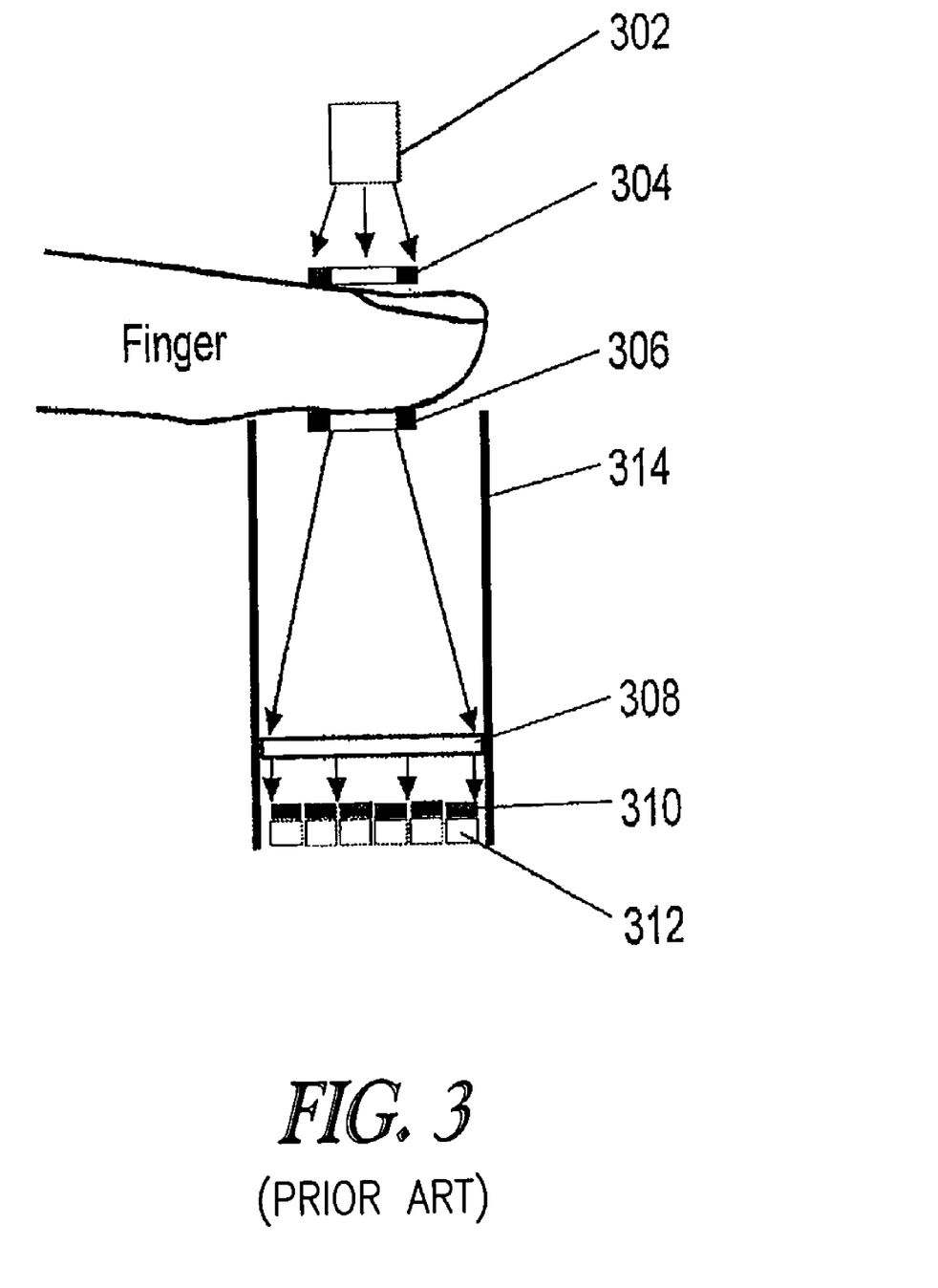
FIG. 3 illustrates an existing optical configuration for performing optical measurements of a biological sample, according to some embodiments.

Referring now to FIG. 3, the configuration of a conventional apparatus for measuring the amount of light absorbed by a human finger. An Infrared Emitting Diode ("IRED") block 302 includes a plurality of IREDs that generate near infrared ("NIR") radiation or light beams from 850 nm to 1100 nm. The generated NIR light beams enter an entrance aperture 304 and pass through the finger. The NIR light beams transmitted through the finger pass through an exit aperture 306 onto a lens 308. The lens 308 collimates light beams and projects them onto filter array 310 and then detector array 312. The apparatus also includes a wall housing 314 to prevent stray light from reaching the light detectors.

In this optical configuration, the light beams passing through the exit aperture 306 are completely mixed in wavelength. More specifically, the entire light power distribution from 850 nm to 1100 nm is transmitted to every detector in the detector array 312.

As described below, there are issues with the device configuration depicted in FIG. 3 that hamper the effectiveness of the device and that result in the potential high baseline noise.

Low Light Illumination Power

To accommodate small finger size of children, light should enter the finger through an entrance aperture 304 having a diameter of approximately 0.25 (¼) inches or less, and that the light transmitted through the finger should be collected through an exit aperture 306 having a diameter of approximately 0.25 (¼) inches or less. However, the number of IRED that can be placed into a 0.25-inch diameter area is limited. For example, only four 3 millimeter (mm) diameter IREDs can be effectively placed into the 0.25-inch diameter area of the entrance aperture 304. Because the average power from each IREDs is about 2.5 milliwatts (mW) with fifteen (15) to twenty (20) degrees half power emission angle, the total usable power that enters the finger from each IRED is approximately fifty percent (50%), or 1.25 mW. Thus, for four (4) IRED, the total usable power is approximately five (5) mW (e.g., 4×2.5 mW×0.50) for the entire wavelength range covered by the four IREDs, typically 850 nm to 1100 nm.

Absorption and Scattering by Human Finger

In general, as described above, the light that enters the finger will be attenuated by skin, fat, muscle, blood, and bone. For example, it has been observed that absorption and scattering of light by the human finger can reduce the power of transmitted light within the NIR region of 850 nm to 1100 nm by a factor of approximately 200. As a result, the total IR power transmitted through the finger is approximately only 25 microwatts (µW) (e.g., 5 mW/200) in the entire wavelength region covered by the four IREDs, typically 850 nm to 1100 nm.

Small Collection Solid Angle by Coupling Optics

Light is emitted from the exit aperture 306 in all directions in the $2\pi$ solid angle beneath the finger. In conventional optical designs it is difficult to collect most light power transmitted through the finger because the exit aperture 306 cannot be treated as a point source. Typically, the total light power collected using optical layout shown in FIG. 3 is only about 10%, or a power reduction by a factor of 10 to 2.5 µW within the entire wavelength region covered by the four IREDs, typically 850 nm to 1100 nm. Note that this is the optical power sent to all detectors in FIG. 3.

Number of Detectors

Moreover, optical systems such as shown in FIG. 3, may require as many as twenty (20) to thirty (30) diode detectors to obtain accurate information regarding chemical components in blood. Therefore, the light power goes to each detector will be about 125 nW or less.

Narrow Band-Pass Filter

The interference filter placed on top of each detector typically has a full width at half maximum (FWHM) bandwidth of 10 nm, which reduces the light power by a factor of 25 to 5 nW, assuming a uniform power distribution across the entire wavelength region from 850 nm to 1100 nm. Furthermore, the peak transmittance of each interference filter is about 50% or less. Accordingly, the light power received by each detector is reduced to about 2.5 nW or less.

Photoelectric Conversion Efficiency

The photoelectric conversion efficiency for Silicon Diode detectors ranges from 0.1 amps/watts (A/W) at 1100 nm to about 0.5 A/W at 900 nm. As a result, depending on the center wavelength of the corresponding interference filter, the photocurrent produced by each detector is between 0.25 nanoamps or less (nA) to 1.25 nA or less for each detector. The corresponding high end shot noise, within 10 Hz bandwidth, is about $2.0 \times 10^{-4}$ Absorbance (p-p) or larger, which is over a factor of 6 of what is required for accurate determination of the value of $\Delta A$, as defined by equation (5), with an S/N ratio of 100. In other word, to reach the desirable S/N ratio of 100:1 for $\Delta A$, light power received by the detectors should be increased over 40 folds.

Figure 4:
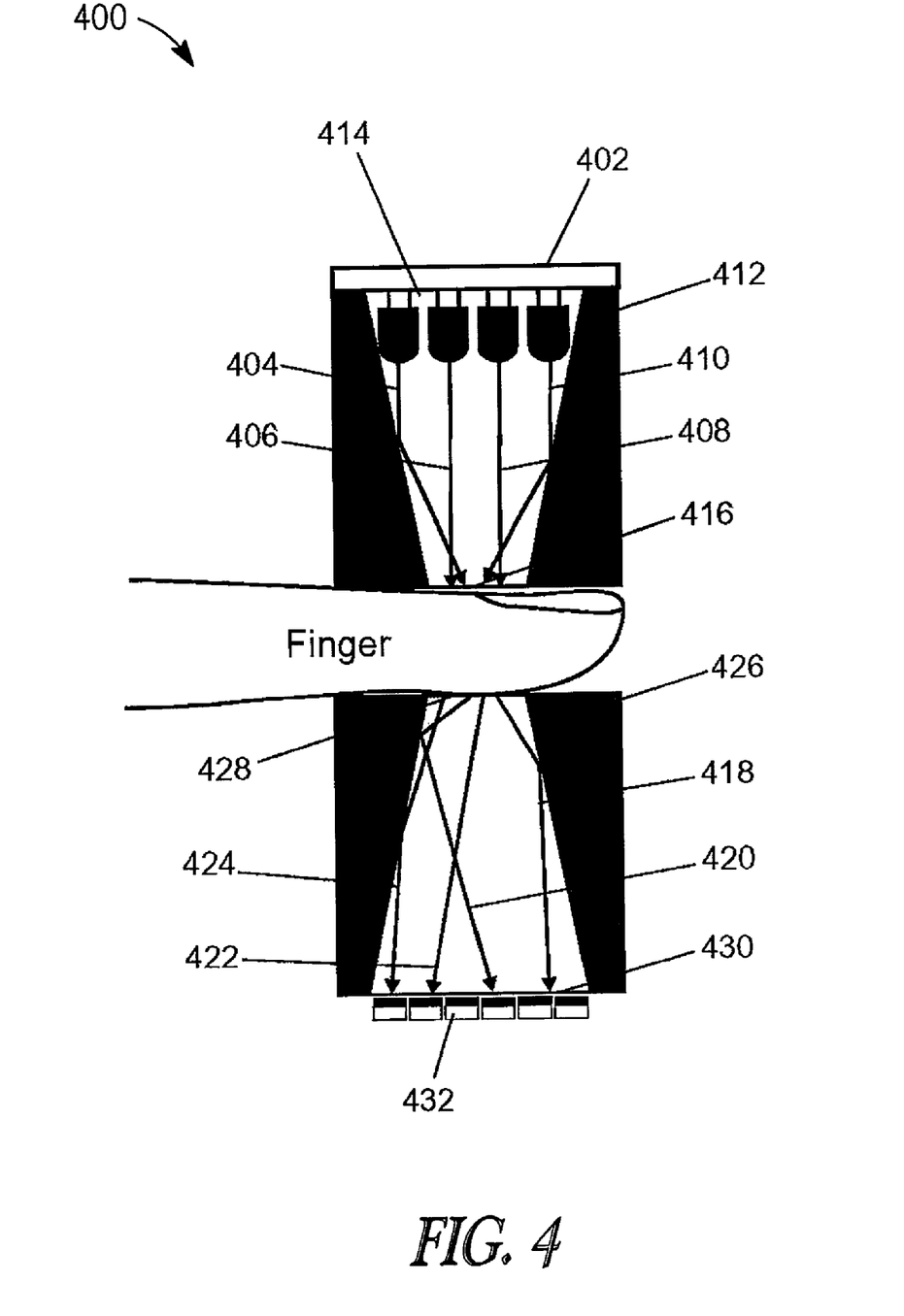
FIG. 4 illustrates an optical configuration for performing optical measurements of a biological sample, according to some embodiments.

FIG. 4 illustrates an optical configuration for performing optical detection of a biological sample according to one aspect of the present optical measurement system 400. A light source 402 generates a plurality of light beams 404, 406, 408, 410. The light source 402 may be incandescent light sources or infrared emitting diodes, for example. According to one aspect of the optical measurement system 400, each of the light beams 404, 406, 408, 410 have a different wavelength or a different wavelength range. For example, the first light beam 404 may have a wavelength range between 850-920 nanometers ("nm"), the second light beam 406 may have a wavelength range between 900-980 nm, the third light beam 408 may have a wavelength between 970-1050 nm, and the fourth light beam 410 may have a wavelength between 1030-1100 nm. The total wavelength range may include from about 800 nm to about 1200 nm, for example. Although the optical measurement system 400 is described herein as generating four (4) light beams, it is contemplated that the light source can be altered to generate fewer light beams or additional light beams in other embodiments.

The light beams 404, 406, 408, 410 from the light source 402 enter a light illumination funnel 412 through an entrance opening 414 and exit the light illumination funnel 412 through an exit opening 416. The diameter of the exit opening 416 of the light illumination funnel 412 is smaller than or equal to the diameter of the entrance opening 414. For example, according to one embodiment the diameter of the entrance opening 414 is approximately 0.625 (⅝) inches and the diameter of the exit opening 416 is approximately 0.25 (¼) inches. Accordingly, in contrast to the configuration depicted in FIG. 3, the light illumination funnel 412 focuses the light beams 404, 406, 408, 410 in the same general direction toward the top of the finger of a user. The light illumination funnel may significantly increase the total light power received by the target area in comparison to the configuration of FIG. 3, and therefore substantially increase the Signal-to-Noise Ratio.

Figure 5:
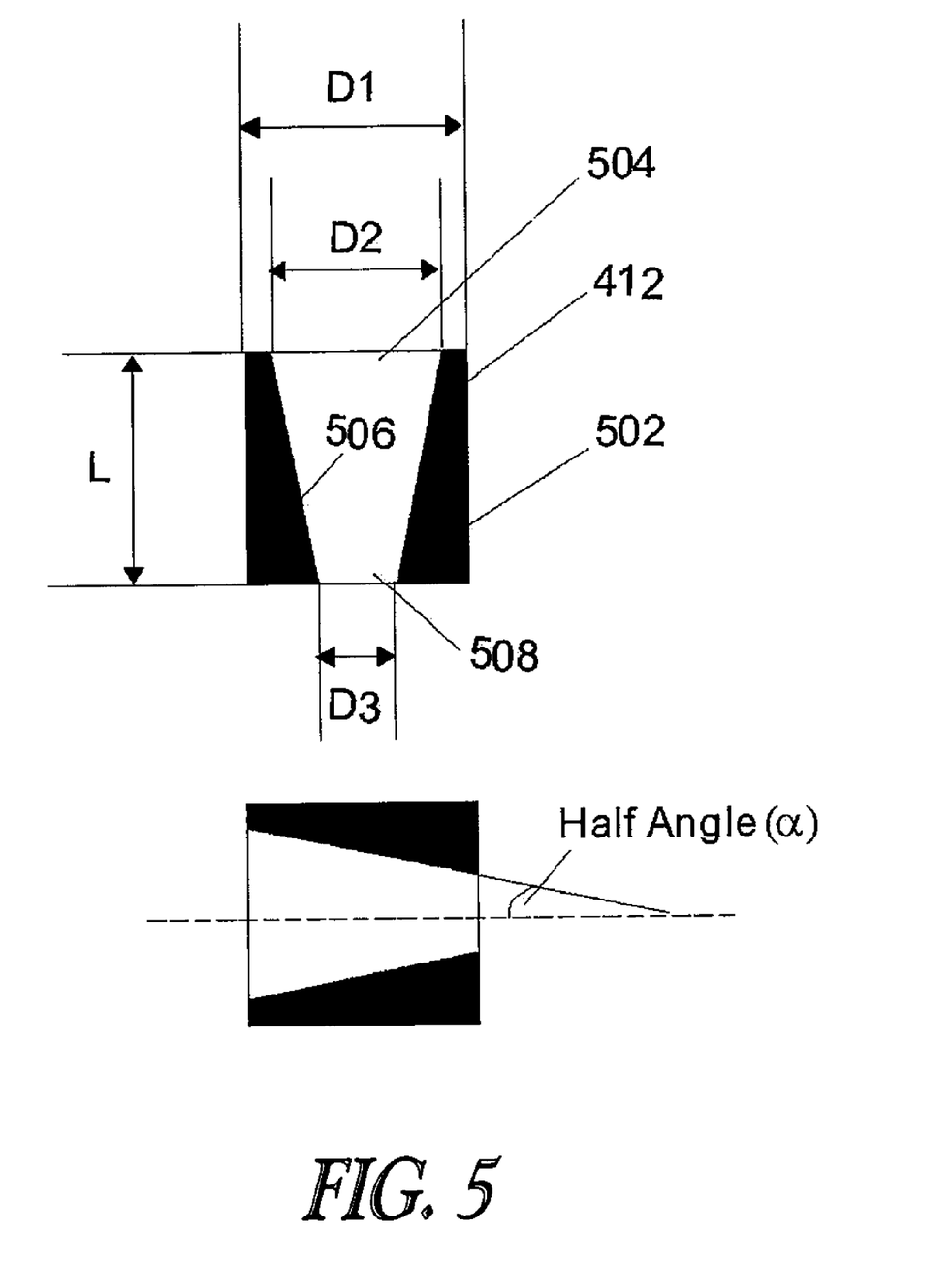
FIG. 5 illustrates a cross sectional view of a light funnel, according to some embodiments.

FIG. 5 depicts a cross sectional view of the light illumination component or funnel 412. According to one aspect, the light illumination funnel 412 has a substantially cylindrical outer wall 502 with diameter D1, and a first opening 504 defined by an inner wall 506 that is of a frusto-conical shape and two light entrance/exit openings 508 and 504. The opening 508 (second opening) has a smaller diameter, D3, and opening 504 (first opening) has a larger diameter, D2. The separation distance between the two light openings is L, and the Half Angle of the frusto-conical shape of the inner surface is α. According to one embodiment of the invention the value of Half Angle α ranges from 10 to 15 degrees. The Half Angles may be less than about 25 degrees, for example. The light illumination funnel 412 may be formed from plastic, metal or other suitable material or compound/layers of material, with any desired refractive index(es). According to one aspect, the light illumination funnel 412 is formed from metal and the surface of inner wall 506 is made highly reflective. When configured properly, the light intensity at the exit 508 may be increased by a factor of 50 to 100 over the light intensity at the entrance 510.

Figure 6:
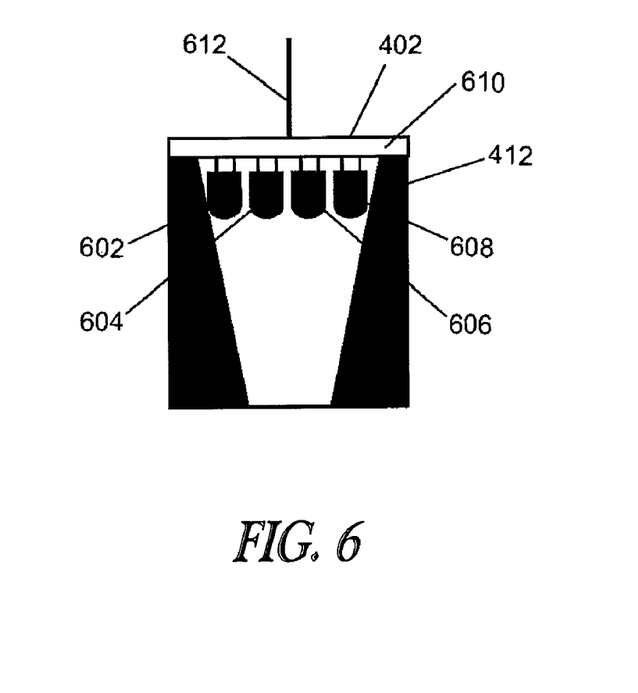
FIG. 6 illustrates components of the light source, according to some embodiments.

FIG. 6 depicts components of the light source 402 according to one aspect of the optical measurement system 400. A circuit board may be positioned near or in contact with the first opening of the funnel and may include light sources mounted on or in contact with the board. In one example, a plurality of IREDs 602, 604, 606, and 608 are mounted to a printed circuit board (PCB) 610. The PCB 610 receives electric power through a power line 612 that is connected to a power source (e.g., power source 201) such as a battery. When the electric power is supplied through the power line 612, each of the IREDs 602, 604, 606, and 608 receives power and generates a plurality of light beams (e.g., light beams 404, 406, 408, 410). Notably, IREDs with similar operational current can be connected in series to increase battery life. The light source may be mounted within the funnel or above the funnel, such as by being surrounded by a housing, for example.

According to one aspect, the light illumination funnel 412 may be mounted to the PCB 610 via screws, posts or other connecting means. The frusto-conical shape of the inner surface of the light illumination funnel 412 serves to concentrate and focus the light beams 404, 406, 408, 410 from the IREDs 602, 604, 606, 608 into a generally conical beam toward the finger.

Figure 7:
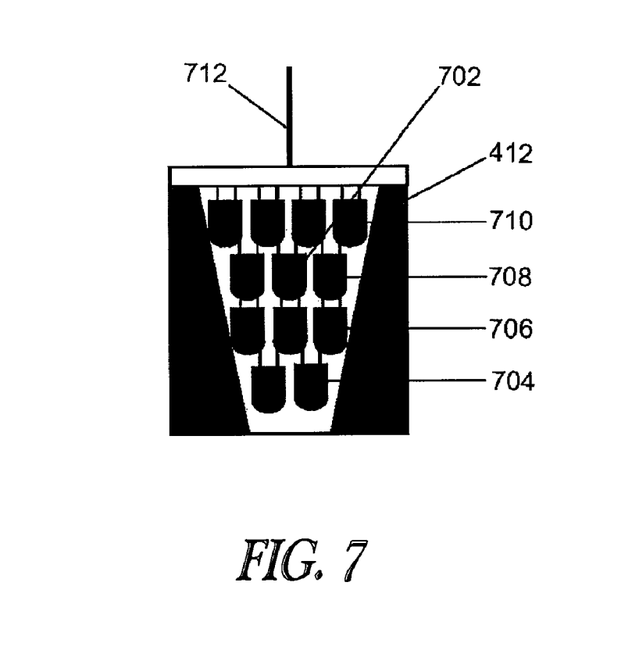
FIG. 7 illustrates a cross-sectional view of a light funnel with an infrared emitting diode (IRED) array matrix disposed therein, according to some embodiments.

FIG. 7 depicts cross-section view of another embodiment of the light illumination funnel 412 with a three-dimensional (3-D) IRED array matrix 702 disposed therein. Multiple light sources, such as IREDs, may be positioned in three-dimensional layers and arranged to optimize light intensity. The light sources may be positioned in horizontal and vertical layers, for example. According to this embodiment, there are a total of twenty six (26) IREDs included in the 3-D array matrix. The IREDs are arranged in four (4) layers. A first row, as indicated by 704, includes four (4) IREDs (two IREDs not shown), a second layer, as indicated by 706, includes five (5) IREDs (two IREDs not shown), a third layer, as indicated by 708, includes seven (7) IREDs (four IREDs not shown), and a fourth layer, as indicated by 710, includes ten (10) IREDs (six IREDs not shown). Power line 712 provides power for all IREDs. According to other embodiments, other IRED patterns may also be utilized. Any number of light sources or layers may be utilized to optimize the light intensity.

Because IREDs are optically transparent to infrared lights, the light loss due to blocking effect within the funnel cavity should be low and the structure shown in FIG. 7 is expect to collect over 85% light power emitted from the IREDs 3-D array in the light funnel cavity. As a result, the total light power transmitted through the 0.25-inch diameter of the exit opening 416 of the light illumination funnel 412 should be approximately 55 mW (e.g., 26×2.5 mW×0.85). Therefore, the total light power transmitted through the 0.25 inch opening above the finger in present optical measurement system 400 is approximately eleven (11) times of the corresponding power reached at the aperture 306 (e.g., 5 mW) of the configuration described in reference to FIG. 3. Moreover, the increased light power received at the finger will increase the amount of light power that can be transmitted through the finger and, thus, increases the light power that can be detected at the detector block 432.

Referring back to FIG. 4, light beams 404, 406, 408, 410 are attenuated by the finger and components of the optical measurement system 400, and, thus, attenuated light beams 418, 420, 422, 424 are emitted from the finger. The attenuated light beams 418, 420, 422, 424 that are emitted from the finger enter a light collection funnel 426 through an entrance opening 428 (first opening) and exit the light collection funnel 426 through an exit opening 430 (second opening). The diameter of the entrance opening 428 of the light collection funnel 426 is smaller than or equal to the diameter of the exit opening 430. For example, according to one embodiment, the diameter of the exit opening 430 is approximately 0.625 (⅝) inches and the diameter of the entrance opening 428 is approximately 0.25 (¼) inches. As a result, the light collection funnel 426 collects attenuated light beams 418, 420, 422, 424 more efficiently and distributes them across a detector block 432.

The structure of the light collection funnel 426 may be substantially similar to the structure of the light illumination funnel 412 depicted in FIG. 5. For example, the light collection funnel 426 has a substantially cylindrical outer wall 502 and a central opening 504 defined by an inner wall 506 that is of a frusto-conical shape. The light funnel collector 426 may also be formed from plastic, metal or other suitable material or compound/layers of material with any desired refractive index(es). According to one aspect, the light collection funnel 426 is formed from metal and the surface of the frusto-conical shape inner wall is made highly reflective. It has been observed that the overall collection efficiency of light collection funnel 426 is over 80%, which is 8 folds of that obtained using traditional optical collection structure shown in FIG. 3. The combination of utilizing a light illumination funnel 412 and light collection funnel 426 may increase the light power received by the finger by about 40 to about 80 times in comparison to the optical configuration in FIG. 3

The detector block 432 is positioned beneath the exit opening 430 of the light collection funnel 426 and comprises a plurality of light-sensing devices (e.g. light sensing devices 228, 230, 232, 234) such as an array of photodiodes. According to one aspect of the optical measurement system 400, each of the light-sensing devices detects a specific wavelength of light as defined by a corresponding interference filter placed on top of the detector.

A processor (e.g., processor 243) can be coupled to the detector block 432 and configured to calculate a change of current signals generated by the light sensing devices. For example, as described above in reference to FIG. 2, the processor 232 executes an algorithm such as shown in equation (5) to calculate the change in the light absorption (ΔA) solely caused by the blood in the finger. Thereafter, this quantitative calculation of light absorption of the blood can be used to determine a characteristic of the blood.

Embodiments of the invention may also include methods of using a light illumination funnel, light collection funnel or apparatus described herein. A light source may contact a target through an illumination funnel, sufficient to generate transmitted, transflected or reflected light. The transmitted, transflected or reflected light may enter a light collection funnel and be directed to one or more detectors, for example.

What is claimed is:

1. A light illumination funnel, comprising:
   a first opening, positioned to receive an incoming light source;
   a second opening, positioned opposite the first opening and with a diameter smaller than the first opening;
   inner reflective walls, in contact with the first opening and second opening;
   wherein the funnel is of frusto-conical shape and has a half angle of less than 25 degrees; and
   a passage for receiving a biological sample located directly below the second opening.

2. The light illumination funnel of claim 1, wherein the funnel has a half angle of about 10 to about 15 degrees.

3. The light illumination funnel of claim 1, further comprising a printed circuit board positioned near or in contact with the first opening, wherein the printed circuit board is in contact with at least one light source positioned near the first opening.

4. The light illumination funnel of claim 1, further comprising a plurality of light sources positioned near the first opening.

5. The light illumination funnel of claim 4, wherein the plurality of light sources are in contact with a printed circuit board positioned near or in contact with the first opening.

6. The light illumination funnel of claim 4, wherein the light sources comprise infrared emitting diodes.

7. The light illumination funnel of claim 4, wherein the light sources are positioned in a three dimensional arrangement.

8. The light illumination funnel of claim 7, wherein the three dimensional arrangement comprises light sources positioned in horizontal and vertical layers.

9. The light illumination funnel of claim 4, wherein the light sources comprise incandescent light sources.

10. A light collection funnel, comprising:
    a first opening, positioned to receive an incoming sample light source;
    a second opening, positioned opposite the first opening and with a diameter larger than the first opening;
    inner reflective walls, in contact with the first opening and second opening;
    wherein the funnel is of frusto-conical shape;
    a passage for receiving a biological sample located directly above the first opening; and
    at least one light detector below the second opening.

11. The light collection funnel of claim 10, further comprising one or more detectors positioned near or in contact with the second opening.

12. The light collection funnel of claim 10, wherein the at least one light detector comprises a detector array.

13. The light collection funnel of claim 10, further comprising one or more filters, gratings or lenses positioned between the funnel and the at least one light detector.

14. An apparatus, comprising:
    a light source configured to generate a plurality of light beams;
    a light illumination funnel, of frusto-conical shape, for collecting the plurality of light beams through an entrance opening having a first diameter and for focusing and directing the plurality of light beams to a target area through an exit opening having a second diameter, wherein the second diameter is less than the first diameter;
    a light collection funnel, of frusto-conical shape, for collecting the plurality of light beams emitting from the target area at a second entrance opening having a third diameter and for directing the plurality of light beams through a second exit opening having a fourth diameter, wherein the third diameter is less than the fourth diameter;
    a passage for receiving a biological sample located at the target area between the light illumination funnel and light collection funnel;
    a detector comprising a plurality of light-sensing devices each configured to detect a light beam directed through the second exit opening and to generate an output signal indicative of the power of light detected; and
    a processor for analyzing the output signal and generating measurement data.

15. The apparatus of claim 14, wherein the light source comprises one or more light emitting diodes.

16. The apparatus of claim 15, wherein the wavelength range comprises differing wavelength ranges between about 800 nm and 1200 nm.

17. The apparatus of claim 14, wherein the light source is positioned at the entrance opening of the light illumination funnel.

18. The apparatus of claim 14, wherein the light source comprises one or more incandescent light sources.

19. The apparatus of claim 14, further comprising one or more filters, gratings or lenses positioned between the light collection funnel and the detector.

20. The apparatus of claim 14, further comprising a plurality of interference filters each configured to pass a different one of the plurality of light beams directed through the second exit opening as a function of wavelength range, wherein the plurality of interference filters are positioned between the light collection funnel and the detector.

21. The apparatus of 20, wherein each of the plurality of light-sensing devices are configured to detect a light beam of a specific wavelength or wavelength range as defined by the corresponding interference filter from the plurality of interference filters through which the light beam passed.

* * * * *